United States Patent [19]

Cardon et al.

[11] Patent Number: 5,383,892
[45] Date of Patent: Jan. 24, 1995

[54] STENT FOR TRANSLUMINAL IMPLANTATION

[75] Inventors: Alain Cardon, Rennes; Yvon Kerdiles, Saint Gregoire; Michel Boliveau, Cesson Seuigne; Denis Ansel, Thorigne-Fouillard; Jean Debuigne, Chantepie, all of France

[73] Assignee: Meadox France, Bievres, France

[21] Appl. No.: 972,977

[22] Filed: Nov. 6, 1992

[30] Foreign Application Priority Data

Nov. 8, 1991 [FR] France .................. 91 13820

[51] Int. Cl.⁶ ................................ A61F 2/04
[52] U.S. Cl. .......................... 606/198; 623/1; 623/12
[58] Field of Search ............. 606/108, 191, 194, 198; 623/1, 11, 12

[56] References Cited

U.S. PATENT DOCUMENTS

| | | | |
|---|---|---|---|
| 4,733,665 | 3/1988 | Palmaz | 623/1 |
| 4,740,207 | 4/1988 | Kreamer | 623/1 |
| 5,064,435 | 11/1991 | Porter | 623/12 |

FOREIGN PATENT DOCUMENTS

| | | |
|---|---|---|
| 0183372 | 6/1986 | European Pat. Off. . |
| 0274846 | 7/1988 | European Pat. Off. . |
| 0335341 | 10/1989 | European Pat. Off. . |
| 0421729 | 4/1991 | European Pat. Off. . |
| 8700442 | 1/1987 | WIPO . |

*Primary Examiner*—Stephen C. Pellegrino
*Assistant Examiner*—M. Peffley
*Attorney, Agent, or Firm*—Bucknam and Archer

[57] ABSTRACT

A stent consisting of the alternate juxtaposition of axially rigid cylindrical parts and at least one axially flexible cylindrical part. The stent comprises two axially rigid cylindrical parts at its two ends, the axially rigid cylindrical parts being adapted to expand radially in plastic manner and the axially flexible cylindrical part or parts being adapted to expand radially in elastic manner. Such a stent is of axially modulable length and flexibility.

7 Claims, 2 Drawing Sheets

STENT FOR TRANSLUMINAL IMPLANTATION

FIELD OF THE INVENTION

The present invention relates to new stents for transluminal implantation and in particular new vascular stents.

BACKGROUND OF THE INVENTION

Stents for transluminal implantation (also called "expandable intraluminal graft") have been developed these last few years. They are metallic supports which are inserted into a part of the human body, (such as the bile ducts, the urinary system, the digestive tube, . . . ) and notably by percutaneous route, inside the blood vessels, generally the arteries (in which case they are called vascular stents). The supports are adapted to expand radially. They are inserted while they have a first diameter ($d_1$) and implanted, in the desired area, for example inside the vessel, and expanded in situ, until they reach a second diameter ($d_2$:$d_2 > d_1$). An angioplasty balloon, associated to a catheter, can be used to expand them radially.

Several types of stents are known, and in particular so-called "flexible" stents, such as those described in Patent Applications FR-A-2 525 896 and EP-A-0 183 372 and so-called "rigid" stents, such as those described in Patents U.S. Pat. Nos. 4,739,762 and 4,776,337 or in Patent Applications EP-A-0 221 570 and EP-A-0 364 787.

SUMMARY OF THE INVENTION

The present invention proposes a novel type of stents, which could be called "mixed" since they combine flexible parts with rigid parts. The combination according to the invention of flexible parts and rigid parts in the structure of a stent, is not any kind of combination.

The stent for transluminal implantation, according to the present invention, consists of the alternate juxtaposition of axially rigid cylindrical parts and at least one axially flexible cylindrical part; said stent comprising axially rigid cylindrical parts at its two ends; said axially rigid cylindrical parts being capable of expanding radially in plastic manner, while said axially flexible cylindrical part or parts is or are adapted to expand radially in elastic manner.

The alternate juxtaposition of the flexible parts and of the rigid parts is such that there are always:
 one axially rigid part at each end of the stent;
 two axially rigid parts on either side of an axially flexible part.

Such an arrangement enables the stents according to the invention to fasten securely to the walls of the parts of the human body in which they are implanted and minimizes the risk of disturbances in the flow of the fluids circulating in the parts of the human body.

The stents according to the invention can exist in many embodiments. Indeed, the number of alternations of rigid parts and flexible part or parts can be varied.

It is possible to have one flexible part between two rigid end parts or several flexible parts and at least one intermediate rigid part between two rigid end parts.

According to two preferred embodiments of the invention, the structures of the stents follow the sequences indicated hereinbelow:

1) rigid end part-flexible part-rigid end part

R-F-R 2) rigid end part-flexible part-intermediate rigid part-flexible part-rigid end part

R-F-R'-F-R

For reasons of symmetry of deformation and of automatic production, the rigid intermediate parts are preferably identical to the rigid end parts (R=R'). This however is not a requirement.

In a general way and for the reasons given hereinabove, the stents according to the invention advantageously have rigid parts (end part and intermediate part or parts) which are all identical as well as equally identical flexible parts. This, nevertheless, does not exclude stents of more asymmetrical structure from the scope of the invention.

Depending on the total length and on the axial flexibility required for a stent according to the invention, it is possible to vary:
 the intrinsic characteristics of the rigid and flexible parts, notably their length, and
 the number of alternations (rigid part/flexible part).

The invention therefore proposes "articulated" stents, of modulable length and axial flexibility.

The flexible part or parts and the rigid parts of the stents are joined together by welding.

They must therefore be made from materials which can be welded together. It is moreover obvious that such materials have to be biocompatible, and each one should have the required mechanical properties (elasticity for the flexible part, plasticity for the rigid part).

For the rigid part, it is recommended to use stainless steel (and in particular of 316 L type) or titanium (in particular of T 35 ot T 40 type). These materials have, in the annealed state, an equivalent and wide enough plasticity range. Any other biocompatible metal (or metal alloy) with similar mechanical properties can also be used.

One or more flexible parts in titanium which shows good elastic properties, such as the T 60 type, are advantageously combined with rigid parts in titanium. Similarly, one or more flexible parts in a stainless steel which has the required elasticity and which may or may not have undergone suitable thermal and/or mechanical treatments, are advantageously combined with rigid parts in stainless steel.

Whatever the case, the axially flexible parts which are liable to expand radially in elastic manner are parts which expand radially while keeping the material of which they are made within its elastic deformation range.

As indicated hereinabove, the stents according to the invention always have rigid ends. They can also include intermediate rigid parts in their structure. The rigid—intermediate or end-parts—help the stent to be positioned, and in particular, once expanded, they ensure its anchoring, whatever happens.

The anchoring is advantageously improved by giving to said rigid parts shapes such that their ends "curl up" during radial expansion. By deforming so—outward opening—, the ends sink slightly into the wall of the parts of the body where the stent is implanted, hence improving the anchoring. Such improved anchoring makes it possible to minimize the turbulences, inherent to the presence of the stent, in the blood flow for example, if the stent is implanted in a blood vessel.

The axially rigid parts of the stents according to the invention can be given several shapes; shapes which, when produced in the adequate material, allow the expected radial expansion and induces the aforementioned "curling up".

For example, the axially rigid cylindrical parts can consist of tubes, along the generating lines of which are regularly distributed "slots" and "half-slots"; said "half-slots" being spilt and issuing into the ends of said tubes, thus creating flanges on which the axially flexible cylindrical parts are advantageously fixed.

The flanges—T-shaped ends—deform outwardly during the expansion and are advantageously used for interlocking the flexible part or parts and the rigid parts. They ensure, by their very shape and deformation, an optimum impacting of the stent in the wall of the parts of the body where they are implanted. They offer a safe bearing surface and tend to sink into said wall.

The axially rigid cylindrical parts of the stents according to the invention can therefore consist of tubes along the generating lines of which slots have been cut in. The diameter of the tubes is of course the diameter set for the stent, before radial expansion.

The slots made in the tubes are particularly intended for minimizing the covering rate of the wall of the parts of the body in which they are implanted and for allowing radial expansion.

According to a first embodiment, a full slot—stretching along virtually the whole generating line of the tube—can be provided alternately with a set of two half-slots, separated by a metal strip; said two half-slots being split so as to issue onto the ends of the tube and to create flanges.

According to a second embodiment, and in particular to obtain longer rigid parts, it is possible to provide alternately:

two full slots along a generating line, and
a set of two "half-slots" separated by one full slot along another generating line, the end parts of the half-slots being always split to allow expansion and to form the flanges.

Also, in order to obtain longer rigid parts, it is possible to arrange for this embodiment, to be provided with longer slots.

The slots and "half-slots" are regularly distributed on the periphery of the tube; this in order to obtain a homogeneous deformation throughout the radial expansion.

For the deformation to be perfectly homogeneous, the dimensions and distribution of the slots cut into the tube will be advantageously optimized, so that all the (remaining) metallic parts of said tubes have substantially the same width ($e \approx e' \approx e''$).

The metallic parts of said tube consist of:
the longitudinal strips between two successive sets of slots cut along two generating lines;
the uncut parts between two slots along the same generating line;
the uncut parts between the end of the tube and the split or non-split ends of said slots.

Moreover, according to a preferred embodiment of the invention, all the slots cut into the tube have rounded ends, and no sharp angles. In this way, any risks of incipient cracks, liable to cause splits during expansion, are avoided.

The slots are advantageously in the form of rectangles, which are closed, widthwise, by two half-circles, of diameter equal to their widths (▭). Such slots deform under expansion in order to create "losenges", truncated along their larger diagonal.

The axially rigid cylindrical parts of the stents according to the invention are produced from metallic tubes in which the adequate slots have been cut.

Their covering rate after expansion, should be less than 20%. This figure is a compromise. Obviously, there has to be enough material for the stent to act as a support but not too much for it not to become uncomfortable, in particular, it should not create a risk of thrombosis inside a blood vessel.

Concerning the axially flexible cylindrical parts, these, as already indicated, are always inserted, in the structure of the stents according to the invention, between two axially rigid cylindrical parts. They are the ones which confer to said stents the axial flexibility.

They advantageously consist of a wire meshing, each wire being, by its two ends, welded to the axially rigid cylindrical parts—surrounding the axially flexible cylindrical parts—close to a knot of said meshing.

All the wire ends of the flexible meshing part are fixed to the rigid ends. This prevents the meshing from "coming undone", and avoiding the existence of loose wires, which would either cause an injury to those parts of the human body where the stent is implanted, or on the contrary float about inside said parts and in doing so, create dangerous turbulences.

The ends of the flexible parts—supported under expansion by the rigid parts—are thus stabilized.

The welded connection is performed close to a point to where the meshing wires converge; this in order to reduce to a minimum, the stresses exerted on the welding during expansion.

As a result, the length of the flexible parts can be adjusted to within half-a-mesh. The length of a flexible part between two rigid parts obviously ranges between a minimum length, necessary for obtaining the required elasticity and a maximum length beyond which a risk of the median zone of said flexible part collapsing, is liable to occur.

Advantageously, the wire meshing constituting the flexible parts of the stents according to the invention, is not any type of meshing.

The different flexible and rigid parts of said stents, which are radially expandable, are in fact expanded in situ—inside a blood vessel or any other part of the human body—under the action of an expandable balloon. Such a balloon is made up from a woven structure. In particular, it is possible to use a balloon of polyurethane associated to a dilatation catheter.

Then, the characteristics of the meshes constituting the flexible parts of the stents according to the invention will be, advantageously, placed in coincidence with the meshes of the woven structure of the expandable balloon. By mesh characteristics are meant:
the natural angle of slope (before expansion),
the aperture angle (after expansion); angles measured in relation to the longitudinal axis of the assembly;
the behavior under expansion.

The coincidence ensures a synchronous axial displacement between the balloon and the stent, during expansion, thereby eliminating any relative sliding of one with respect to the other. It also guarantees the absence of all unwanted axial deformation when the stent is inserted in position.

Therefore, the axially flexible cylindrical parts of the stents according to the invention, advantageously consist of a metallic wire meshing spreading helically from one axially rigid cylindrical part to the next axially rigid cylindrical part.

The axially flexible cylindrical parts covering rate is generally around that of the axially rigid cylindrical parts; it is below 20% and preferably around 15%.

The wires of the flexible parts are welded to the rigid parts, in order to, as indicated hereinabove, reduce to a minimum the stresses and the extra thickness at their level. Advantageously, the weldings are located in the least deformable zone of the flanges constituting the ends of the rigid parts. They are made on the outer parts of said flanges.

DESCRIPTION OF THE PREFERRED EMBODIMENT

According to a preferred variant of the invention, the stent comprises:
- axially rigid cylindrical parts, which consists of tubes along the generating lines of which are regularly distributed slots and "half-slots", said "half-slots", which are split, issuing onto the ends of said tubes and, in doing so, creating flanges;
- at least one axially flexible cylindrical part, which consists of a wire meshing; the wires of said meshing being, in the vicinity of a knot thereof, welded in pairs, one at each end of said flanges, one forming a right-hand helical thread line, the other forming a left-hand helical thread line.

BRIEF DESCRIPTION OF THE DRAWINGS

The invention will now be described with reference to the appended FIGS. 1 to 4.

Said figures show a stent comprising an axially flexible cylindrical part (2) between two axially rigid cylindrical parts (1, 1'). Said rigid parts (1, 1') comprise slots (3) and "half-slots" (4), split in (5).

Figure 1:
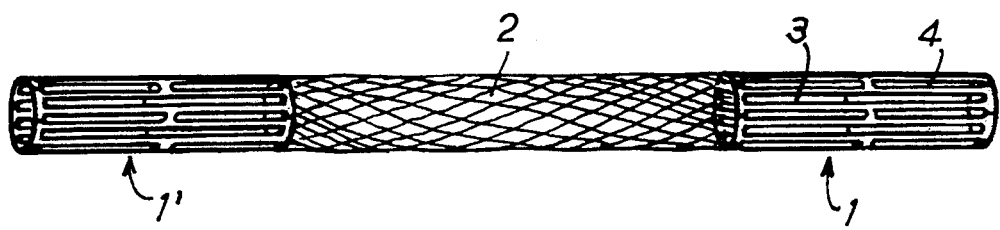
FIG. 1 is a perspective view of a stent according to the invention, non-expanded.
Figure 2:
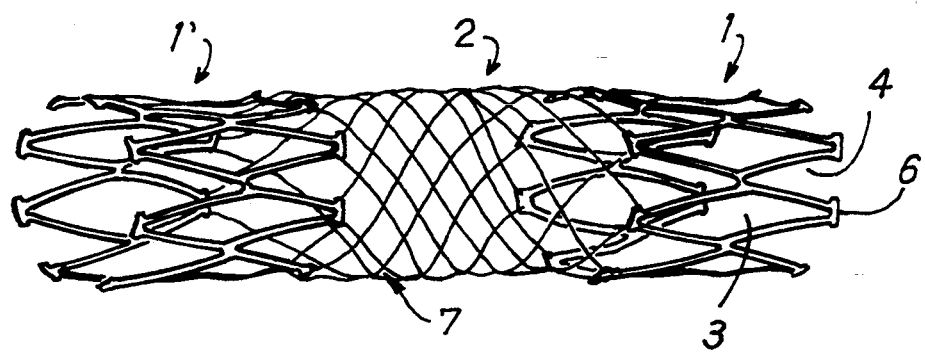
FIG. 2 is a perspective view of the same stent, expanded.
Figure 3:
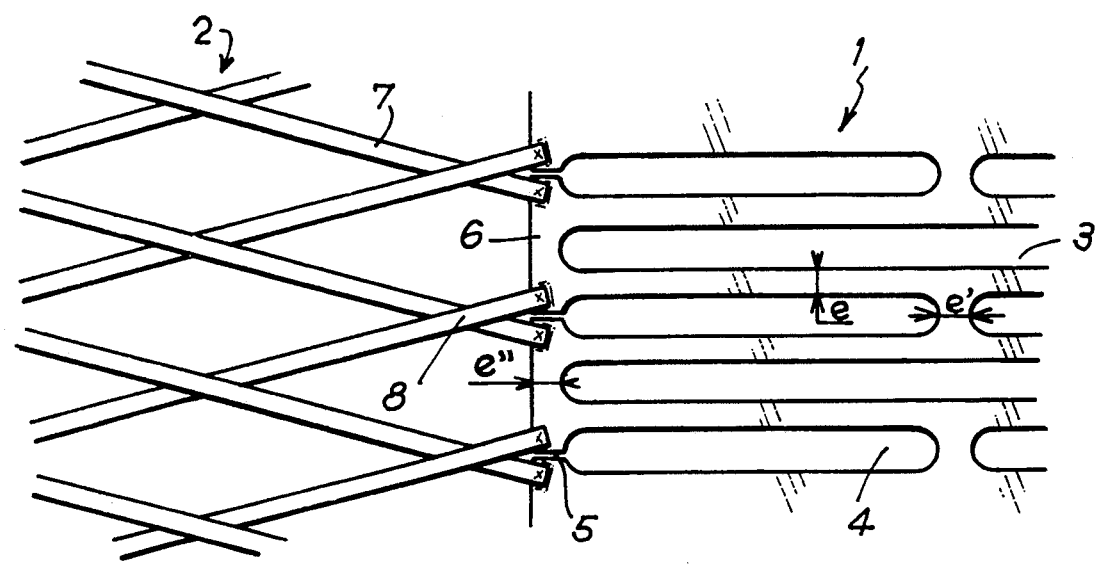
FIG. 3 is a partial front view of a flexible part/rigid part welding zone of the stent according to FIG. 1 (in non-expanded condition).
Figure 4:
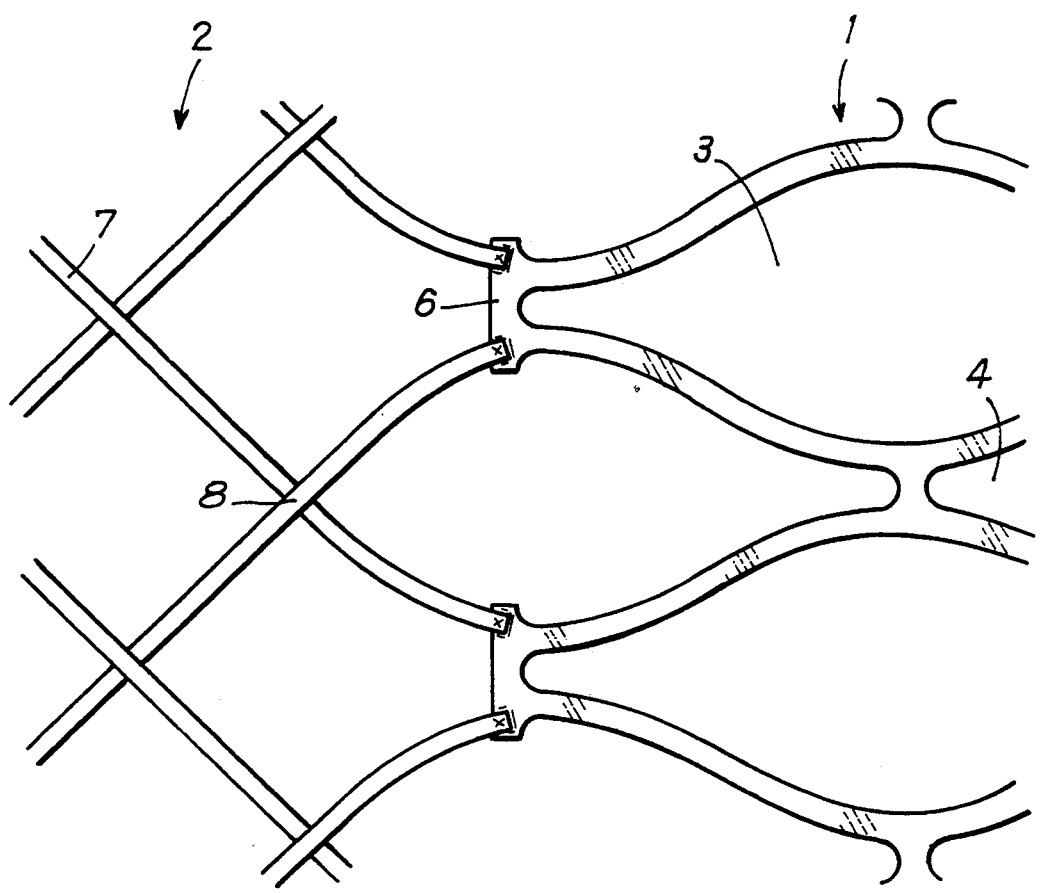
FIG. 4 shows the same zone, in expanded condition.

In (6) are shown the flanges created by such slots (3 and 4). All said slots have rounded ends. More particularly, FIG. 3 shows that the solid metallic parts of the tubes, constituting the rigid ends of the stent, all have substantially the same width:

$$e \approx e' \approx e''$$

The axially flexible cylindrical part (2) is a meshing of wires (7) of cylindrical section. Said wires are criss-crossed to form knots (8). They are welded close to said knots (8), in pairs, on the ends of the flanges (6) of the rigid parts (1, 1').

An example of the possible dimension of such a stent is given hereinbelow:
- length of the rigid end parts: about 8 mm
- length of the flexible median part: between 7 and 21 mm
- initial diameter: 3 mm
- diameter after expansion: 9 mm.

The rigid end parts comprise 8 full slots on their periphery (8 "losenges" after expansion).

The uncut metallic parts—which are left after the slots have been cut—of the rigid end parts have a rectangular cross-section (between about 0.2×0.15 and 0.3×0.2 mm, depending on the width of the slots and on the thickness of the tube).

The rigid parts have a covering rate less than 20% after expansion.

The median flexible part is constituted of wires of diameter between about 0.15 and 0.20 mm. Given the number of full slots of the rigid end parts and consequently the number of flanges (6), on which are welded said wires, the meshing is constituted by the criss-crossing of 8 wires forming right-hand helical thread lines with 8 wires forming left-hand helical thread lines. Depending on the length wanted for the flexible median part (between 7 and 21 mm), said wires make a quarter or three-quarters of a turn. The angle of said wires, measured with respect to the axis of the whole assembly is about 15° before expansion (preangularity), and 45° after expansion.

Such a flexible part has a covering rate around 15%.

We claim:

1. A stent for transluminal implantation having two axes and consisting of an alternate juxtaposition of at least two axially rigid cylindrical parts and at least one axially flexible cylindrical part; said stent having said at least two axially rigid cylindrical parts at said two ends; said at least two axially rigid cylindrical parts being made of a first material having a first structure and being capable of radial expansion in a plastic manner and said at least one axially flexible cylindrical part being made of a second material having a second structure and being capable of radial expansion in an elastic manner, said first and second material being the same material, said first and second structures being different, said first structure of said at least two axially rigid cylindrical parts consisting of tubular members, said tubular members having a longitudinal axis, two ends and a surface, slots and half-slots being cut regularly along said surface and being aligned with said longitudinal axis of said tubular members, said half-slot being split and issuing into said ends of said tubular members whereby flanges are formed, said second structure of said at least one axially flexible cylindrical part consisting of a mesh of wires, said wires being criss-crossed to form knots whereby pairs of wires issue from each knot, said flanges having ends; each wire of each pair being welded to each end of said flanges, whereby a right-hand helical thread line and a left-hand helical thread line are formed.

2. The stent according to claim 1 which includes at least one intermediate axially rigid cylindrical part; said axially rigid intermediate cylindrical part being identical to said two rigid cylindrical parts located at said ends of said stent.

3. The stent according to claim 1 wherein said axially rigid cylindrical parts and said axially flexible part are welded together.

4. The stent according to claim 1, wherein said axially rigid cylindrical parts have ends and said ends curl up during their radial expansion.

5. The stent according to claim 1 wherein uncut parts are left in said tubular members and said slots and half-slots have dimensions and distribution and said dimensions and distribution are such that said uncut parts of said tubular members all have substantially the same width.

6. The stent according to claim 1 wherein said slots and half-slots have rounded ends.

7. A device for the implantation of a stent, comprising a stent according to claim 1, an angioplastic expandable balloon and a catheter, said expandable balloon being made of a second mesh of woven structure, said first mesh of said at least one axially flexible part having a first natural angle of slope, a first aperture angle, a first behavior under expansion, said second mesh of said expandable balloon having a second natural angle of slope, a second aperture angle and a second behavior under expansion which coincide with said first natural angle of slope, said first aperture angle, and said first behavior under expansion.

* * * * *